US00PP28094P3

(12) United States Plant Patent
Ranney

(10) Patent No.: US PP28,094 P3
(45) Date of Patent: Jun. 13, 2017

(54) ***VIBURNUM* PLANT NAMED 'NCVR1'**

(50) Latin Name: *Viburnum×rhytidophylloides*
Varietal Denomination: NCVR1

(71) Applicant: Thomas Green Ranney, Arden, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 56 days.

(21) Appl. No.: 14/545,794

(22) Filed: Jun. 19, 2015

(65) Prior Publication Data

US 2016/0374241 P1 Dec. 22, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

PUBLICATIONS

UPOV hit on *Viburnum* named 'NCVR1', CA PBR 14-8429, published Oct. 31, 2014.*

* cited by examiner

*Primary Examiner* — Anne Grunberg
(74) *Attorney, Agent, or Firm* — Cassandra Bright

(57) ABSTRACT

A new and distinct *Viburnum* cultivar plant named 'NCVR1' is disclosed, characterized by dark green, evergreen leaves. Plants are compact and produce abundant white flowers in Spring. The new variety is a *Viburnum* normally produced as an outdoor garden or container plant.

3 Drawing Sheets

Latin name of the genus and species: The Latin name of the novel plant variety disclosed herein is *Viburnum×rhytidophylloides.*

Variety denomination: The inventive seedling of *Viburnum×rhytidophylloides* disclosed herein has been given the varietal denomination 'NCVR1'.

BACKGROUND OF THE INVENTION

The present invention comprises a new and distinct *viburnum* cultivar hereinafter referred to by the cultivar name 'NCVR1'. This new *viburnum* was developed through a breeding program at North Carolina State University, Mills River, N.C. 'NCVR1' was selected from a population of open-pollinated seedlings of *Viburnum×rhytidophylloides* 'Alleghany' (unpatented). The first asexual propagation of 'NCVR1' was carried out in July 2009 by rooting stem cuttings at the North Carolina State University, Mountain Horticultural Crops Research Station, Mills River, N.C. and has been asexually reproduced repeatedly by vegetative cuttings over a 4 year period. 'NCVR1' roots readily from softwood cuttings treated with a basal dip of 4,000-5,000 ppm indole butyric acid (potassium salt) in water. 'NCVR1' has been found to retain its distinctive characteristics through successive asexual propagations.

SUMMARY OF THE INVENTION

The following are the unique combination of characteristics of this new cultivar when grown under standard horticultural practices at North Carolina State University, Mountain Horticultural Crops Research Station, Mills River, N.C.

1. Compact plant habit.
2. Dark, glossy, evergreen leaves.
3. Abundant white flowers in Spring.

COMPARISION WITH COMMERCIAL VARIETIES

'NCVR1' is similar in most horticultrual characteristics to *Viburnum* 'Willowwood', unpatented. The new variety however differs in the following:

1. 'NCVR1' has dark green foliage, this comparator has light green foliage.
2. 'NCVR1' has a round shaped inflorescence, 'Willowwood' has a flat topped inflorescence.
3. 'NCVR1' has narrower foliage than this comparator.

'NCVR1' can also be compared to *Viburnum* 'Dart's Duke', unpatented. The new variety however differs in the following:

1. 'NCVR1' has larger flowers than 'Dart's Duke'.
2. 'NCVR1' has glossier foliage than 'Dart's Duke'.

COMPARISON WITH COMMERCIAL CULTIVARS

'NCVR1' is distinguished from *Viburnum×rhytidophylloides* 'Alleghany' in that 'NCVR1' has a smaller, more compact form to 120-180 cm tall and wide, whereas *Viburnum×rhytidophylloides* 'Alleghany' will grow larger than 300 cm tall and wide. 'NCVR1' has coriaceous, dark evergreen foliage that is held through the winter (USDA 6B), whereas *Viburnum×rhytidophylloides* 'Alleghany' is deciduous to semi-evergreen.

BRIEF DESCRIPTION OF THE DRAWINGS

This new *Viburnum* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *viburnum*.

DETAILED BOTANICAL DESCRIPTION

Figure 1:
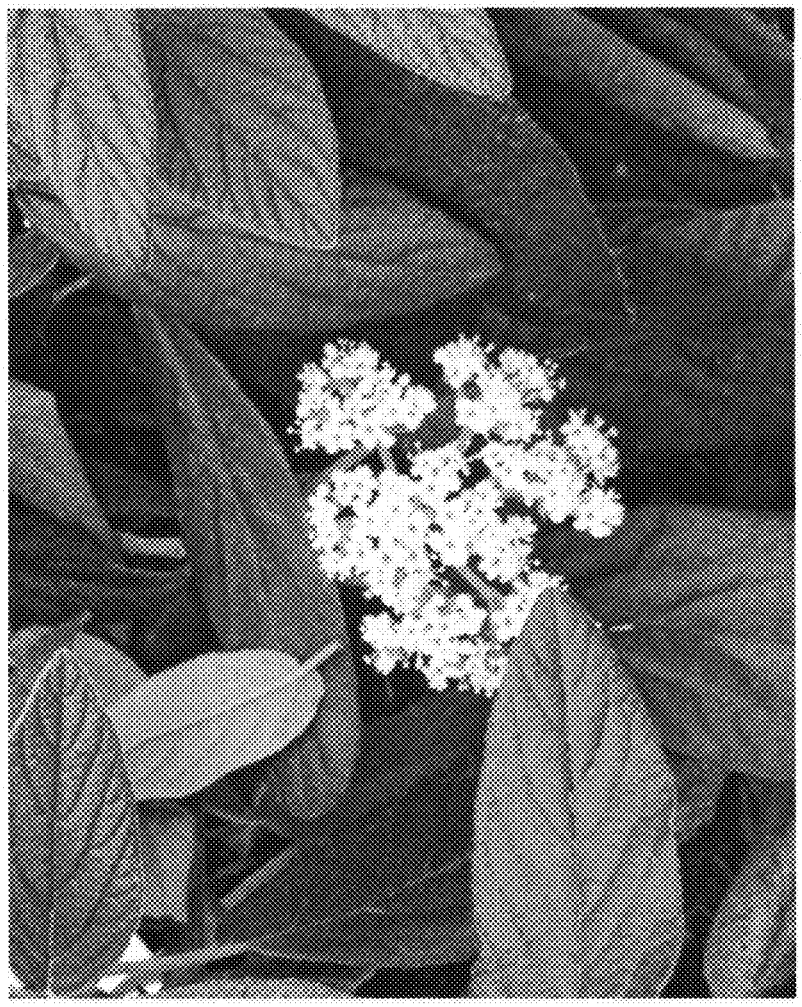
FIG. 1 Photograph showing white inflorescences against dark green foliage of 'NCVR1' taken in April, 2014 in Mills River, N.C.
Figure 2:
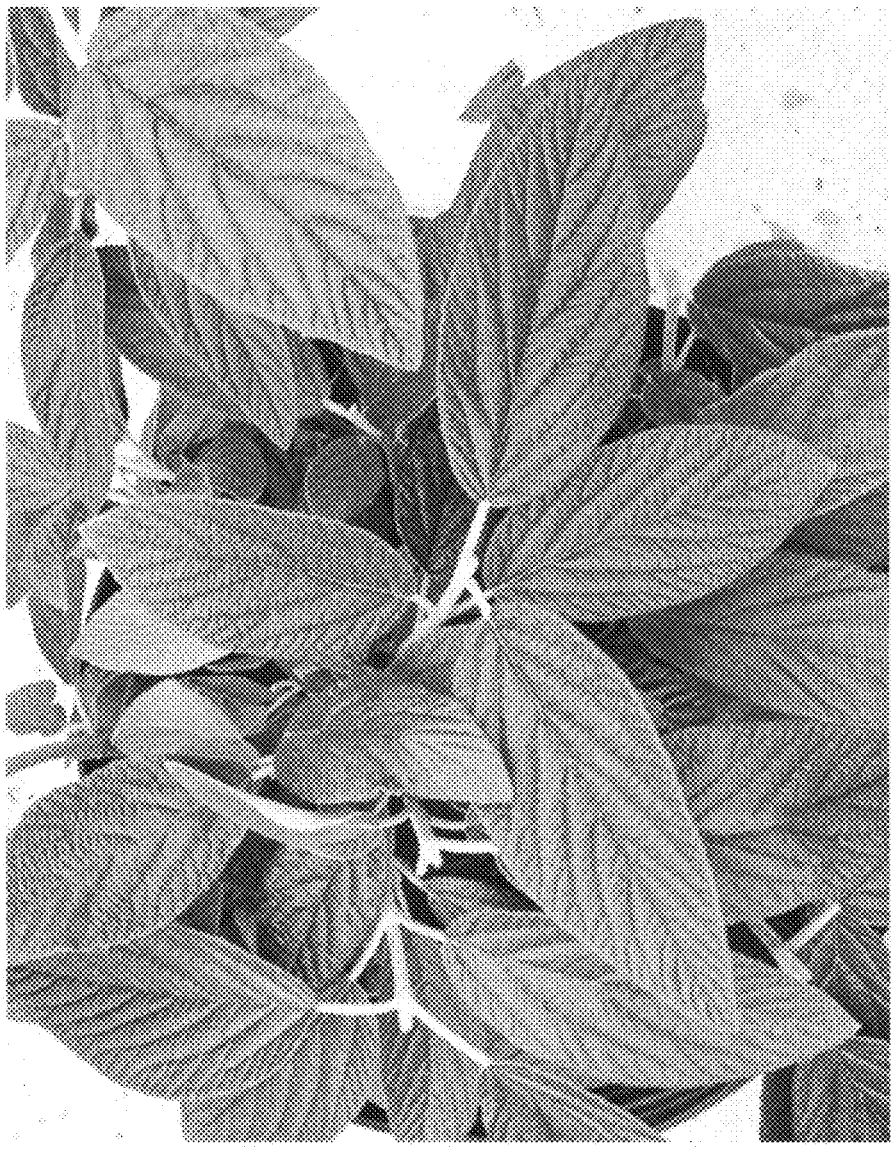
FIG. 2 Photograph showing the foliage of 'NCVR1' taken in April, 2014 in Mills River, N.C.
Figure 3:
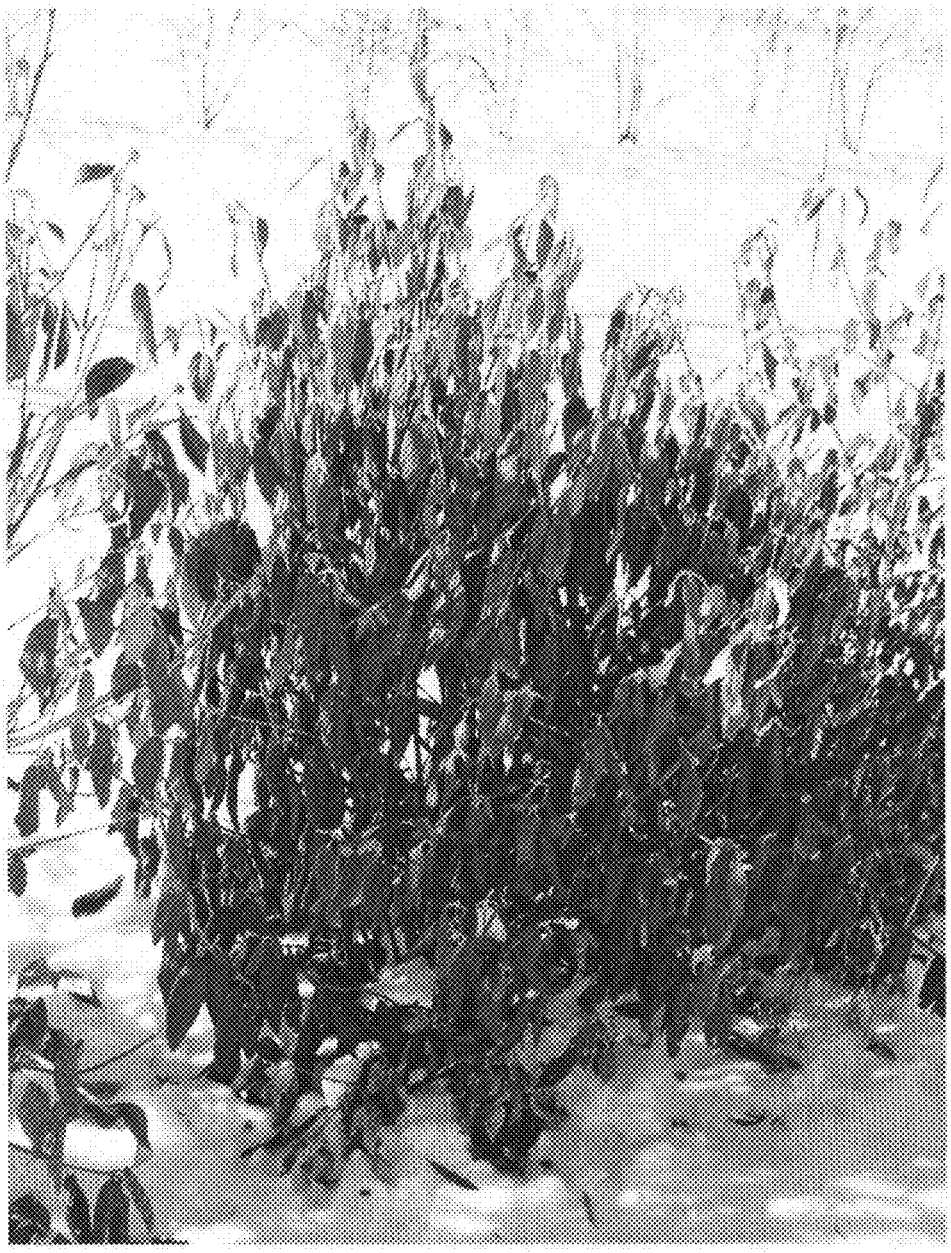
FIG. 3 Photograph showing the form and winter foliage of 'NCVR1' taken in December 2010 in Mills River, N.C.

The following is a detailed description of the botanical characteristics of the new and distinct *viburnum* variety plant known by the denomination 'NCVR1'. The detailed description was taken on a three-year-old, container-grown plant in Mills River, N.C. in 2014. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety

Classification:

*Botanical name.*—*Viburnum* 'NCVR1'.

*Common name.*—*Viburnum.*

Parentage: Selected from a population of open-pollinated seedlings of *Viburnum* ×*rhytidophylloides* 'Alleghany' (unpatented).

Plant description:

*Growth habit.*—Densely branched, upright to oval.

*Height.*—120 to 180 cm.

*Width.*—80 to 120 cm.

Shoot and stem:

*Lateral branch length.*—Avg. 30 cm (typical range: 15 to 50 cm).

*Lateral branch diameter.*—Avg. 0.7 cm (typical range: 0.3 to 1.0 cm).

*Internode length.*—Avg. 8 cm (typical range: 5 to 11 cm).

*Immature shoot texture* (*current year*).—Extremely tomentose.

*Immature shoot color* (*current year*).—Greyed-White (156A).

*Mature stem texture* (*from prior year*).—Glabrous, with lenticels.

*Mature stem color* (*from prior year*).—Brown (200D).

Leaves:

*Type.*—Simple.

*Persistence.*—Semi-evergreen to evergreen.

*Arrangement.*—Opposite.

*Shape.*—Ovate-lanceolate.

*Apex.*—Acute.

*Base.*—Subcordate to oblique.

*Venation.*—Pinnate.

*Vein color.*—Upper: Yellow-Green (146C). Lower: Greyed-Green (194B).

*Margins.*—Entire or obscurely denticulate.

*Emerging leaves.*—Color: Upper: Green (143A). Lower: Yellow-Green (148D). Texture: Sparsely pubescent above and extremely pubescent below.

*Mature leaves during growing season.*—Color: Upper: Yellow-Green (147A). Lower: Greyed-Green (191A). Texture: Rugose, coriaceous, sparsely pubescent above and extremely pubescent below. Length of lamina: Avg. 10 cm (typical range: 6 to 15 cm). Width: Avg. 4 cm (typical range: 2.6 to 5.2 cm).

*Leaf attachment.*—Petiolate.

*Petiole.*—Length: Avg. 1.2 cm (typical range: 0.8 to 1.5 cm). Diameter: Avg. 0.2 cm (typical range: 0.15 to 0.3 cm). Color: Yellow-Green (148C). Texture: Highly pubescent.

Inflorescence:

*Description.*—Single salverform flowers arranged on terminal cymes.

*Number of true flowers per inflorescence.*—75 to 400.

*Flowering season.*—Mid-April to early May in Mills River, N.C.

*Fragrance.*—Slight fragrance.

*Inflorescence.*—Diameter: 12 cm. Height: 4 cm.

*Flower.*—Diameter: 0.5 cm. Height: 0.4 cm.

*Bud.*—Shape: Round. Length: About 0.1 cm. Diameter: About 0.1 cm. Color: White (155B).

*Petals.*—Number: 5 fused petals. Arrangement: Whorled. Length: 0.2 cm. Width: 0.1 cm. Shape: Oblong. Margin: Entire. Apex: Obtuse. Texture: Glabrous. Color: White (155D).

*Sepal.*—Number: 5. Arrangement: Whorled. Length: Less than 0.1 cm. Width: Less than 0.1 cm. Shape: Acute. Margin: Entire. Apex: Acute. Base: Fused. Texture: Slightly glabrous. Color: Yellow-Green (146D).

*Peduncle.*—Length: About 4 cm. Diameter: 0.2 cm. Texture: Very pubescent. Color: Close to Yellow-Green (152B).

*Pedicels.*—Length: About 0.1 cm. Diameter: Less than 0.1 cm. Texture: Pubescent. Color: Green (143C).

Reproductive organs:

*Gynoecium.*—Pistil number: 1. Pistil length: Less than 0.1 cm. Stigma shape: Rounded, three-lobed. Stigma color: Greyed-Orange (172A). Style length: Less than 0.1 cm. Style color: Greyed-Orange (172A).

*Androecium.*—Stamen number: 5. Anther shape: Oblong. Anther size: Less than 0.1 cm. Anther color: Yellow (8A). Amount of pollen: Little to moderate. Pollen color: Yellow (8A).

OTHER CHARACTERISTICS

Fruit and seed: None observed.

Disease and insect resistance: No significant disease or insect pests have been observed.

Cold hardiness: At least USDA zone 6b; testing has not been completed in colder zones.

What is claimed is:

1. A new and distinct *Viburnum* plant named 'NCVR1' as illustrated and described herein.

* * * * *